US012214102B2

(12) United States Patent
McCooke et al.

(10) Patent No.: US 12,214,102 B2
(45) Date of Patent: Feb. 4, 2025

(54) MONITORING DEVICE (71) Applicant: RANDOX LABORATORIES LTD, Crumlin (GB)

(72) Inventors: Catherine McCooke, Crumlin (GB); Peter Fitzgerald, Crumlin (GB)

(73) Assignee: RANDOX LABORATORIES LTD, Crumlin (GB)

( * ) Notice: Subject to any disclaimer, the term of this patent is extended or adjusted under 35 U.S.C. 154(b) by 678 days.

(21) Appl. No.: 17/602,853

(22) PCT Filed: Apr. 9, 2020

(86) PCT No.: PCT/GB2020/050930
§ 371 (c)(1),
(2) Date: Oct. 11, 2021

(87) PCT Pub. No.: WO2020/208363
PCT Pub. Date: Oct. 15, 2020

(65) Prior Publication Data
US 2022/0160921 A1   May 26, 2022

(30) Foreign Application Priority Data

Apr. 12, 2019 (GB) ........................... 1905193

(51) Int. Cl.
*A61L 2/28* (2006.01)
*A61L 2/10* (2006.01)
(Continued)

(52) U.S. Cl.
CPC ....... *A61L 2/28* (2013.01); *A61L 2/10* (2013.01); *G01J 1/429* (2013.01); *G01J 1/44* (2013.01);
(Continued)

(58) Field of Classification Search
CPC .......... A61L 2/28; A61L 2/10; A61L 2202/14; G01J 1/429; G01J 1/44
See application file for complete search history.

(56) References Cited

U.S. PATENT DOCUMENTS

2004/0200975 A1   10/2004   Brown et al.
2012/0056102 A1   3/2012    Stanley et al.
(Continued)

FOREIGN PATENT DOCUMENTS

BE      856088 A        10/1977
CN   103480019 A         1/2014
(Continued)

OTHER PUBLICATIONS

Wikipedia, "Low-pass filter", retrieved from the Internet at: <<https://web.archive.org/web/20151118193209/https://en.wikipedia.org/wiki/Low-pass_filter>>. (Year: 2015).*
(Continued)

*Primary Examiner* — Chih-Cheng Kao
(74) *Attorney, Agent, or Firm* — Banner & Witcoff, Ltd.

(57) ABSTRACT

There is provided a sterilisation monitoring device for a molecular diagnostics analyser. The device comprises a sensor arranged in use to detect radiation; and an analysis unit connected to the sensor. The analysis unit is arranged in use to issue a signal when the radiation level incident on the sensor is lower than a threshold level.

10 Claims, 5 Drawing Sheets (51) Int. Cl.
*G01J 1/42* (2006.01)
*G01J 1/44* (2006.01)

(52) U.S. Cl.
CPC ........ *A61L 2202/11* (2013.01); *A61L 2202/14* (2013.01)

(56) References Cited

U.S. PATENT DOCUMENTS

| | | | |
|---|---|---|---|
| 2014/0341777 A1 | 11/2014 | Deshays et al. | |
| 2016/0114066 A1* | 4/2016 | Lichtblau | A61L 2/10 250/455.11 |
| 2016/0279275 A1* | 9/2016 | Deshays | A61L 2/24 |
| 2018/0369435 A1 | 12/2018 | Dhiman et al. | |

FOREIGN PATENT DOCUMENTS

| | | |
|---|---|---|
| CN | 105268003 A | 1/2016 |
| CN | 105424179 A | 3/2016 |
| EP | 0454488 A2 | 10/1991 |
| WO | 2014/186741 A1 | 11/2014 |
| WO | 2017/090847 A1 | 6/2017 |

OTHER PUBLICATIONS

CN 105763700 A and its English translation (Year: 2015).*
Aspencore, "Active Low Pass Filter", retrieved from the Internet at: <<https://web.archive.org/web/20170704015214/http://www.electronics-tutorials.ws/filter/filter_5.html>>. (Year: 2015).*
Wikipedia, "Comparator", (Mar. 2018), retrieved from the internet at: <<https://web.archive.org/web/20171208034221/https:/en.wikipedia.org/wiki/Comparator>>. (Year: 2018).*
AspenCore, "Op-amp comparator", (Oct. 2017), retrieved from the internet at: <<https://web.archive.org/web/20171011063336/https://www.electronics-tutorials.ws/opamp/op-amp-comparator.html>>. (Year: 2017).*
Oct. 15, 2019—(GB) Search & Examination Report—App. No. 1905193.7.
Jul. 28, 2020—(WO) International Search Report & Written Opinion—App. No. PCT/GB2020/050930.

* cited by examiner

MONITORING DEVICE

CROSS-REFERENCE TO RELATED APPLICATIONS

This application is a U.S. National Stage application under 35 U.S.C. § 371 of International Application PCT/GB2020/050930 (published as WO 2020/208363 A1), filed Apr. 9, 2020, which claims the benefit of priority to United Kingdom Patent Application No. 1905193.7, filed Apr. 12, 2019. Benefit of the filing date of each of these prior applications is hereby claimed. Each of these prior applications is hereby incorporated by reference in its entirety.

FIELD OF THE INVENTION

The present invention relates to monitoring the status of a sterilisation system, which may typically be used in a molecular diagnostics analyser.

BACKGROUND

In many industries there are locations where it is important there is a clean environment. Such locations have various reasons for needing to be sterile, free of contamination or free of bacteria.

There are a number of ways in which the relevant location can be cleaned to the appropriate level, One such way is to use electromagnetic radiation, such as Ultraviolet Type C (UVC) light, to irradiate surfaces to inactivate microorganisms. This is commonly referred to as radiation sterilisation.

The use of radiation sterilisation is common for sterilising equipment used for molecular diagnostic assays. This includes the interior of analysers used to process samples on which an assay is being conducted.

When using UVC light as an electromagnetic radiation source for radiation sterilisation, one or more UVC bulbs are commonly used. As with other electromagnetic radiation sources, UVC bulbs have a lifespan after which they are less effective or ineffective at providing enough UVC irradiation to cause suitable amounts of sterilisation to occur.

The results produced from molecular diagnostic assays have become more sensitive as the techniques used in the assays have been improved. This means limiting contamination has become an increasingly important factor when carrying out an assay. As such, to ensure a suitable level of sterilisation is achieved, each UVC bulb used need to be replaced from time to time.

Conventionally two approaches have been used to determine when a UVC bulb should be replaced. One approach is for the UVC bulb to be replaced as part of the regular service schedule for an analyser. This means that as part of a service, each UVC bulb are replaced, A further approach is for each UVC bulb to be replaced after a predetermined number of hours of use, such as after 10,000 hour of use.

We have found that each of these approaches is inadequate. This is because a UVC bulb may have already started to deteriorate before the service is scheduled to take place, meaning results will be effected. This is also the case when bulb replacement is based on the hours of use.

Conversely, a bulb may have a significant amount of useful lifespan left when the analyser is serviced or when the predetermined number of hours of use has elapsed. This means a bulb will be needlessly replaced, which wastes resources as well as money, therefore having an environmental impact in addition to an economic impact.

To address these issues an improved approach for determining when to replace such a radiation source is needed.

SUMMARY OF THE INVENTION

According to a first aspect, there is provided a sterilisation monitoring device for (for example suitable for) a molecular diagnostics analyser, the device comprising: a sensor arranged in use to detect radiation; and an analysis unit connected to the sensor, the analysis unit being arranged in use to issue a signal when the radiation level incident on the sensor is lower than a threshold level.

We have found that by carrying out this active monitoring of a radiation source during periods when it is in use, instead of the passive methods used previously, it is possible to identify when the radiation source no longer has the ability to achieve a suitable level of sterilisation. This allows the radiation source to be replaced, recharged or re-established in a timely manner relative to when its performance drops towards or below a level that would cause a detrimental effect on any procedure being carried out for which sterilisation was used. Of course, the analysis unit may be arranged to detect radiation level incident on the sensor.

The analysis unit may be able to cause the signal to be issued by any suitable mechanism. Typically the analysis unit comprises a band pass filter. This provides a simple mechanism for issuing a signal by making use of the radiation being detected by the sensor. This is achieved by the output from the sensor when the radiation level is lower than the threshold level by passing the output through the analysis unit and the filter as the signal being issued, but preventing the sensor output from passing through the analysis unit and filter when the radiation level is above (or equal to) the threshold.

The band pass filter may be a low pass filter. This provides a reliable means for allowing a signal to be issued that only depends on the radiation level being below the threshold, and not needing to be higher than a lower cut-off level.

The low pass filter may be an RC filter. This allows the low pass filter to be kept simple by providing the filter in a minimal number of electrical components.

The low pass filter may additionally or alternatively be an active low pass filter. This removes a reliance on the sensor output providing a strong enough signal for that signal to be issued by the analysis unit. This is achieved by the amplification provided by the active low pass filter. Additionally, this provides a more stable filter by reducing the effect of a change in the signal source impedance or in changes in external impedance.

The active low pass filed may be an inverted active low pass filter. This reduces the number of components needed over a non-inverted active low pass filters. This keeps the component count down, simplifying the filter and reducing manufacture costs.

The analysis unit may comprise a comparator. This allows the analysis unit to provide an output as a change of state in the circuit. This reduces the likelihood of a false output being created since the comparator will only provide an output when predetermined conditions are met, avoiding signal leaking through to cause an unwanted output.

The comparator may comprise an op-amp. This allows for a simple setup of the comparator and to make use of electrical signal originating from the sensor, while also allowing for simple signal amplification.

Whether or not the comparator comprises an op-amp, the comparator may be a voltage comparator. This allows for high saturation of signal, due to the high gain of the op-amp even when the input signals differ by a relatively small amount. This means small changes can be detected and still cause a change in output of the analysis unit.

The comparator may be a dual differential comparator. This allows the use of multiple voltage supplies to convert an analogue input to a digital output using a simple mechanism. This keeps component count to a minimum, allowing the comparator to require a minimum amount of space to keep the analysis unit small.

The sensor may be any sensor capable of detecting radiation. Typically, the sensor is a light sensor. This allows the radiation source to be a light emitting source, which reduces how hazardous the radiation source is capable of being to humans, such as a user of an analyser. Additionally, this allows a source to be capable of being activatable and de-activatable in a simple manner, such as in comparison to an X-ray source, microwave source, gamma ray source or beta radiation source, which could all be used as a radiation source.

The light sensor may be any form of light sensor. Typically, the light sensor is an irradiance sensor. This allows the flux of radiation incident on a surface to be measured to take account of the power being transferred to the surface. This therefore allows the strength of the radiation and sterilisation being achieved to be measured.

The threshold may be 110 Watts per minute (W/min) over a period of about 5 minutes (so about 360 seconds). We have found that this threshold provides an appropriate level at which the radiation source should be replaced, recharged or re-established before a detrimental effect on the amount of sterilisation provided occurs while also allowing a sufficient amount of use of the radiation source to make use of that source viable to use.

According to a second aspect, there is provided a system for (for example suitable for) a molecular diagnostics analyser, the system comprising: a sterilisation monitoring device according to the first aspect; and a decontaminator comprising a radiation source, wherein the radiation source is arranged to emit radiation in use in a distribution area, a sensor of the device, said sensor being arranged in use to detect radiation, is positioned in the distribution area so as to receive radiation from the radiation source, an analysis unit of the device being connected to the sensor and being arranged in use to issue a signal when the radiation level incident on the sensor is lower than a threshold level.

As with the first aspect, we have found that by carrying out this active monitoring of the radiation source during periods when it is use, it is possible to identify when the radiation source no longer has the ability to achieve a suitable level of sterilisation. This allows the radiation source to be replaced, recharged or re-established in a timely manner relative to when its performance drops towards levels that would cause a detrimental effect on any procedure being carried out for which sterilisation was used.

The radiation source may be any a source of any form of radiation detectable by the sensor of the sterilisation monitoring device. For example, this may be X-ray radiation, microwave radiation, gamma ray radiation or beta radiation. Typically however, the radiation source may be an ultraviolet type C (UVC) source. This reduces how hazardous the radiation source is capable of being to humans. Additionally, this allows a source to be capable of being activatable and de-activatable in a simple manner.

The UVC source may be a UVC bulb. This allows easy replacement of the radiation source and provides a simple means of providing sterilisation that is able to be activated and de-activated as desired.

According to a third aspect, there is provided a sample analyser for (for example suitable for) conducting a molecular diagnostic assay, the analyser comprising: a processing region; and a system according to the second aspect, the system comprising: a decontaminator comprising a radiation source mounted within the processing region, the radiation source being arranged to emit radiation in use in a distribution area to irradiate at least a portion of the processing region when in use, and a sterilisation monitoring device having a sensor arranged in use to detect radiation, the sensor being located on a surface of the processing region in the at least a portion of the processing region able to be irradiated by the radiation source, the device further having an analysis unit connected to the sensor arranged in use to issue a signal when the radiation level incident on the sensor is lower than a threshold level.

As with the first and second aspects, we have found that by carrying out this active monitoring of the radiation source during periods when it is use, it is possible to identify when the radiation source no longer has the ability to achieve a suitable level of sterilisation. This allows the radiation source to be replaced, recharged or re-established in a timely manner relative to when its performance drops towards levels that would cause a detrimental effect on any procedure being carried out for which sterilisation was used. Additionally, this actively monitorable sterilisation is able to conducted in an analyser in which sensitive procedures, such as assays, are able to be carried out, improving the reliability of the procedure being carried out in the analyser.

There may be a plurality of processing regions. Additionally, whether there is one or more processing regions, each processing region may have one or decontaminators, each with one or more radiation sources; and each processing region may have one or more sterilisation detection monitors.

The (or each) decontaminator may be held stationary within the (respective) processing region. Typically however, the (or each) decontaminator may be moveable within the (respective) processing region. This reduces the likelihood of any part of the processing region from being in a shadowed area where radiation from the radiation source does not penetrate or penetrates to a lesser amount than desired. This therefore improves the ability to provide sterilisation within the processing region.

BRIEF DESCRIPTION OF FIGURES

An example analyser, system and sterilisation monitoring device is described in detail herein with reference to the accompanying figures, of which.

DETAILED DESCRIPTION

Figure 1:
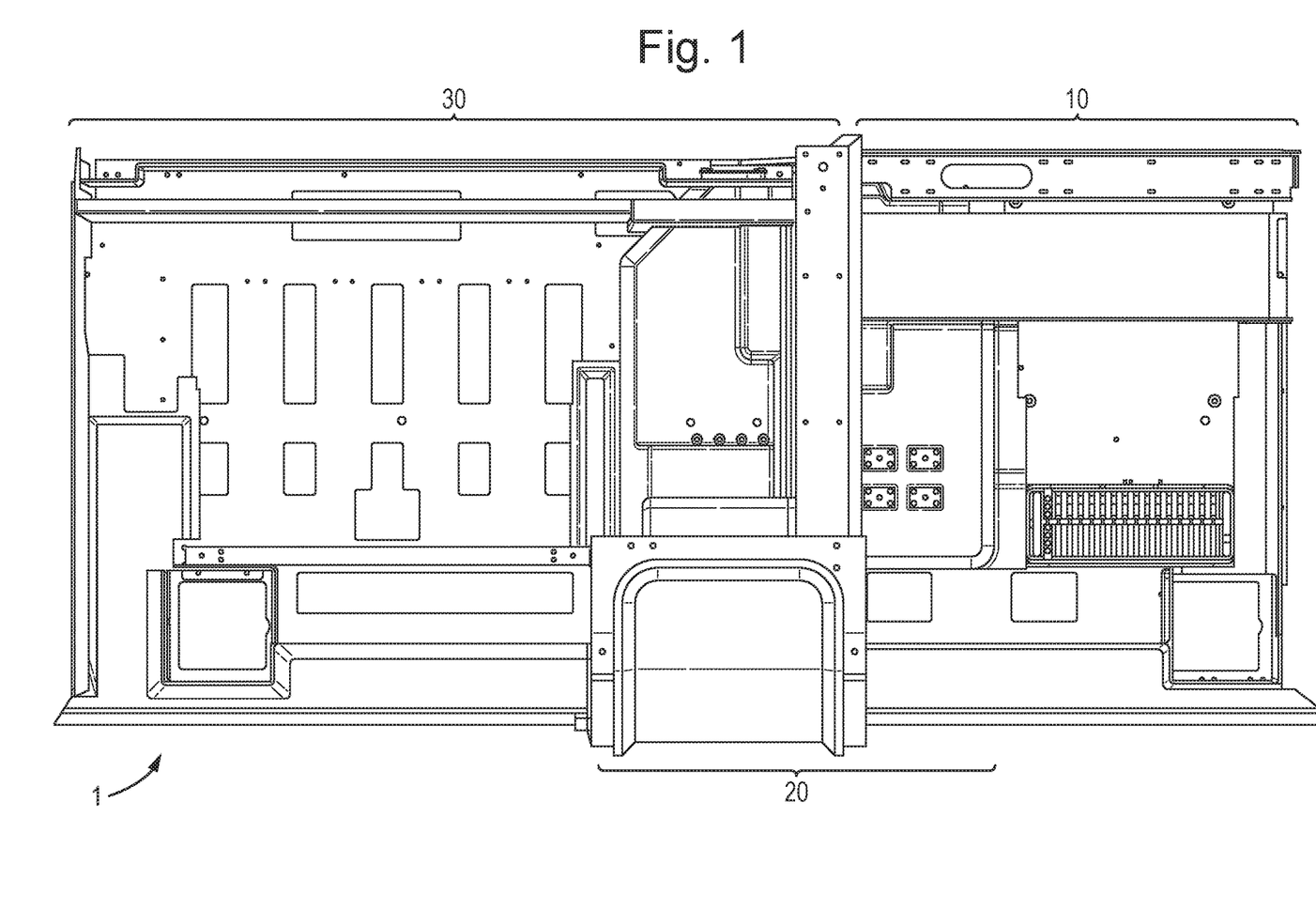
FIG. 1 shows sectional view of an example analyser.

The sterilisation monitoring device described in relation to the figures is used in an analyser, such as the example analyser generally illustrated at 1 in FIG. 1. The analyser is suitable for conducting an assay on fluid or liquid samples. Typically the sterilisation monitoring device is used in relation to an analyser suitable for conducting a molecular diagnostic assay on samples. In such an analyser, the sample is extracted and purified, an amplification process is conducted on the purified sample using PCR and then the constituents of the amplified sample are detected by using various reagents and detection methods.

Figure 3:
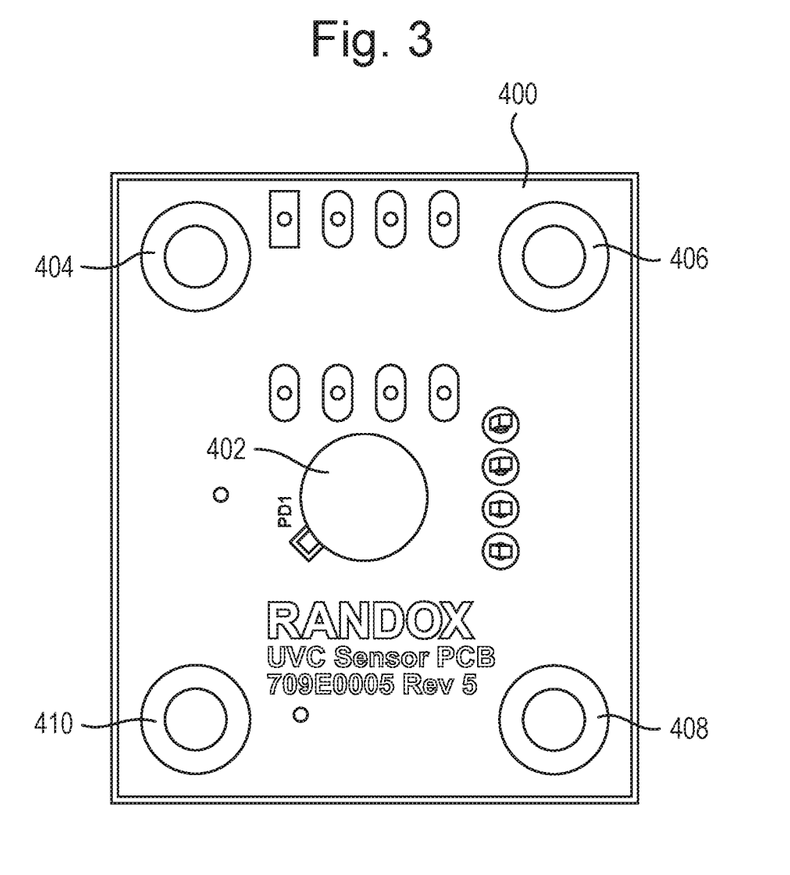
FIG. 3 shows a plan view of an example sterilisation monitoring device.
Figure 4:
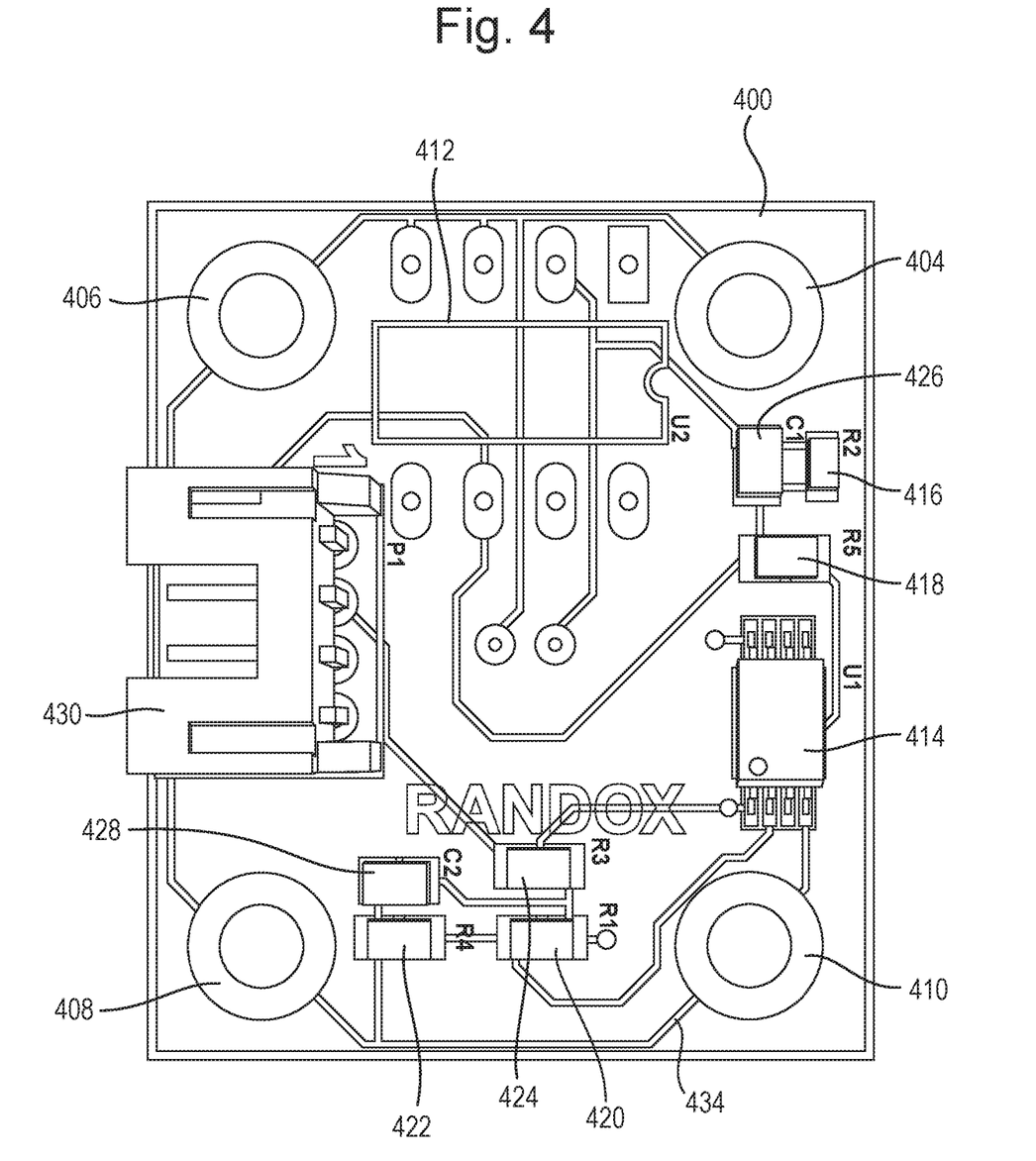
FIG. 4 shows a further plan view of the example sterilisation monitoring device.
Figure 5:
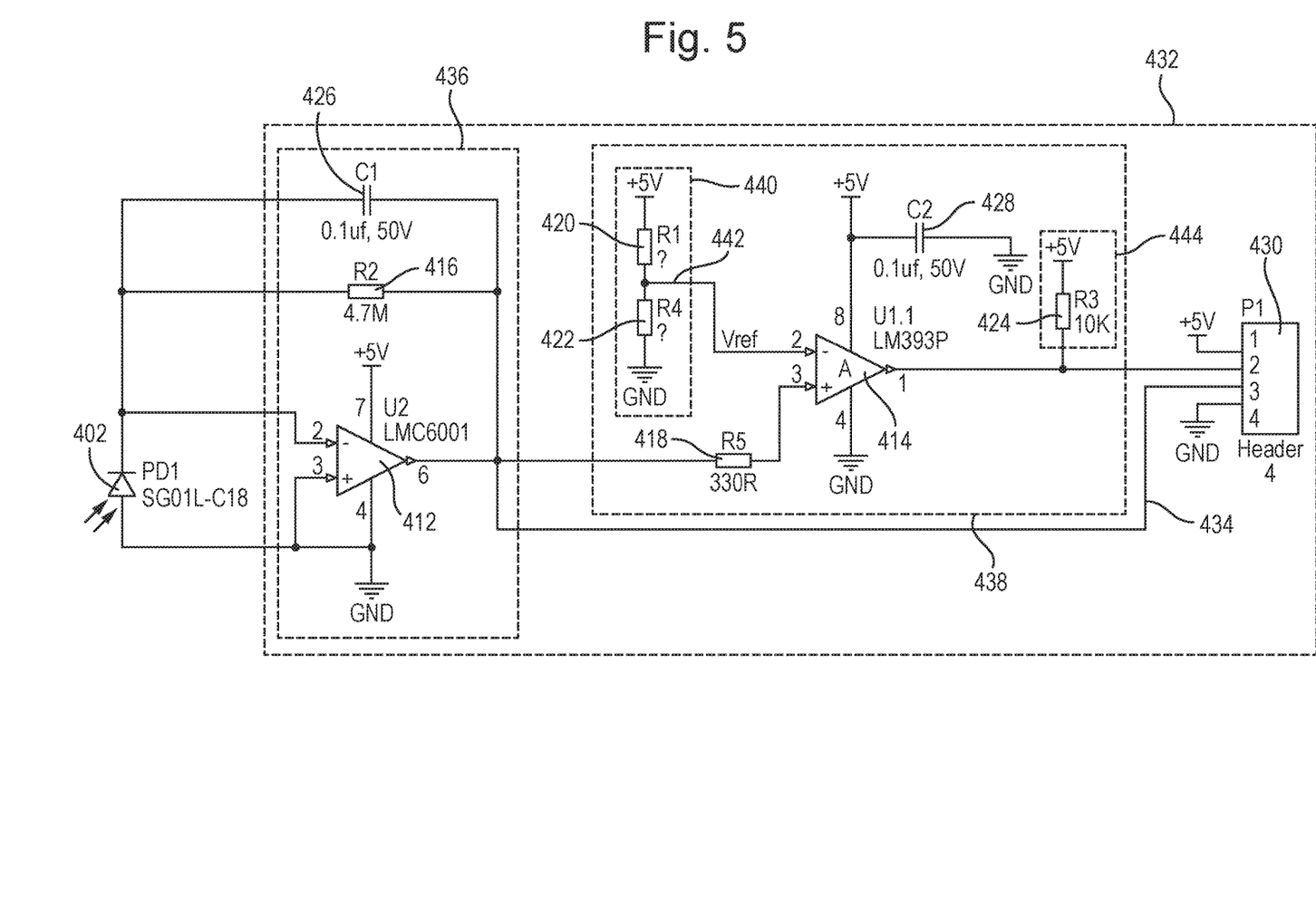
FIG. 5 shows a circuit diagram of the example sterilisation monitoring device.

The analyser is typically separated into different sections where each of the extraction and purification, amplification and detection steps is carried out. Each of these sections provides separate processing regions, extraction and purification being carried out in a first region 10, amplification being carried out in a second region 20 and detection being carried out in a third region 30. One or more sterilisation monitoring devices, such as the example device shown in FIGS. 3, 4 and 5 is able to be located in each of these processing regions. This is because sterilisation is carried out in each of these regions and one or more radiation sources, which are used to provide sterilisation, are provided in each region.

Pipette tips are used to transport fluids within the analyser in the first region 10 and the third region 30. These fluids may be sample fluid, wash, reagents, waste or any other fluid used within the analyser as part of the assay.

Figure 2:
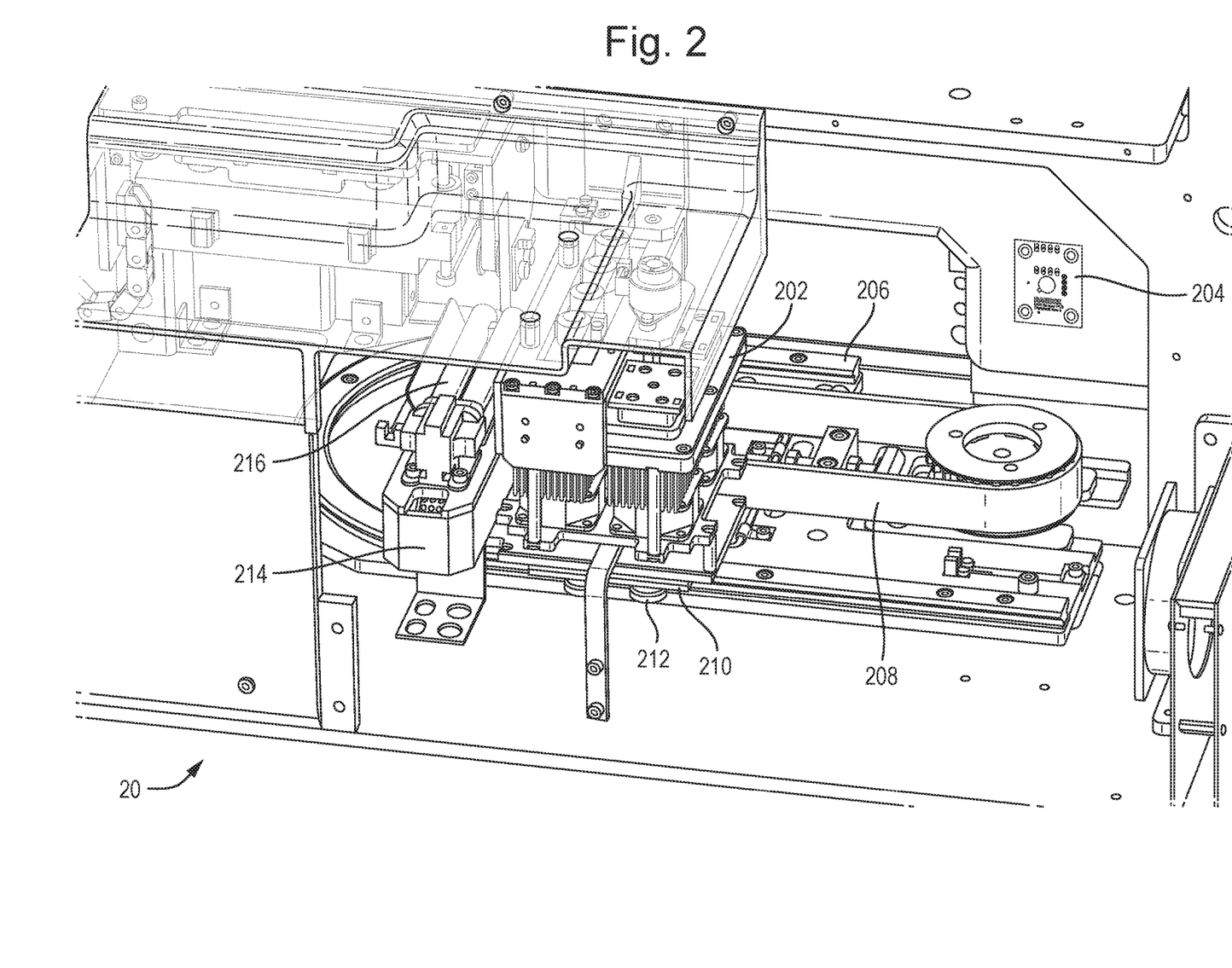
FIG. 2 shows a section view of an example system.

In the first region 10 and the third region 30, the pipette tips are transported connected to pipettors, which are attached to robots, such as a robotic arm (not shown), that provide a programmable translation system for moving components within the analyser. In the second region 20, the fluids are transported in cartridges on a moveable stage 202, which is shown in FIG. 2. In each of these regions, as mentioned above, one or more sterilisation monitoring devices 204 are provided.

FIG. 2 shows an example arrangement of the system used in a molecular diagnostics analyser, such as the analyser 1 shown in FIG. 1, to sterilise and detect the strength of sterilisation being provided.

FIG. 2 shows a second region 20 of an analyser. In the example arrangement shown in FIG. 2, the second region has a moveable stage 202. The moveable stage is moveable along a rail 206 by a belt system 208. This is achieved by the stage being engaged with the belt and having a foot 210 with rollers 212 that engage with the rail.

A decontaminator 214 is attached to the stage 202. The decontaminator has a UVC bulb 216. This acts as an electromagnetic radiation source when the bulb is illuminated. The bulb has a distribution area, which is the region over which, and into which, it emits light. Any surface within this distribution area that has a at least a component orientated towards the bulb and which is not behind another surface or object relative to the bulb (and therefore in shadow) is illuminated by the bulb when in use. Reflection from other surfaces also causes further distribution of light from the bulb.

The bulb is capable of sterilising the surfaces of the second region 20 that fall within the distribution area of the light emitted from the bulb. In other words, sterilisation is achieved when the surfaces are illuminated by the light emitted from the UVC bulb.

The amount of UVC light emitted by the bulb 216 varies during the life of the bulb. We have found that irradiance being provided by the UVC bulb at 110 W/min over a 5 minute period incident on any particular part of a surface is a suitable threshold level. Below this level we have found the quality of sterilisation drops below what may be needed to preform suitable sterilisation. The irradiance is therefore monitored in order to identify when the irradiance drops below this threshold level.

To monitor the irradiance a sterilisation monitoring device 204 is used. In FIG. 2, an example of such a device is shown on a wall of the second region 20 of the analyser 1. This is an example location for the device. In use, the device is located in a position where it will receive a relatively constant amount of radiation when the decontaminator 214 is in use during at least a portion of the time the radiation source is in use. This means the device is not located in a position that is in shadow when the decontaminator is in use. Additionally, the device is positioned away from any locations in the analyser that are likely to have user contact. This is in order to avoid the device becoming damaged by contact with a user. As mentioned above, more than one device may be used in each region.

In the first region 10 and the third region 30 of the analyser, instead of being mounted on a stage, the decontaminator is mounted on one of the robots that provide transport for the pipette tips. This reduces the chances of a part of a surface being predominantly in shadow during use of the decontaminator, and therefore improves the effectiveness of the overall sterilisation provided by the radiation source.

Turning to the sterilisation monitoring device 204, this is shown in FIGS. 3 and 4. The device is based on a printed circuit board (PCB) 400. This supports various electrical components as well as providing the structure to the device itself to allow it to be mounted to a surface within the analyser 1.

As shown in FIG. 3, the PCB 400, in this example, is generally rectangular. In other examples, the PCB may be other shapes, such as square, circular or whatever shape is needed to fit the PCB to the location to which it is to be mounted. In the example shown in FIG. 3, a light sensor in the form of a photodiode 402 is located in the centre of one of the sides of the PCB.

To avoid shadows being cast on the photodiode 402 by other components of the device, the number of other components located on the same side of the PCB 400 as the photodiode is kept to a minimum. In the example shown in FIGS. 3 and 4, the photodiode is the only other electrical component that projects away from the surface of the PCB on which the photodiode is located. There are further features visible on this side of the PCB however. These include power supply terminals 404, 406, 408, 410, and connector pads for components mounted to the opposite side of the PCB.

In this example there are four power supply terminals 404, 406, 408, 410. These provide a connection to ground and a connection to a positive voltage source as appropriate. While the terminals are shown in FIGS. 3 and 4, the connections themselves are not shown.

The opposite side of the PCB 400 to the one on which the photodiode 402 is located is shown in FIG. 4. In this example, two op-amps 412, 414, five resistors 416, 418, 420, 422, 424 and two capacitors 426, 428 and an output connector 430 are located on this side of the PCB. These components make up the analysis unit 432. Of course, in other examples, different components may be provided on this side of the PCB, as well as different numbers of components or each type of component.

Each of the components named above on each side of the PCB 400 form a circuit due to an electrical connection provided by wiring 434 visible on the PCB in FIG. 4. Although any suitable electrical connection means is able to be used, conventionally the electrical connection of each component to the wiring would be provided by a solder joint between a component pin and a pad on the PCB. This conventional means is the means used in the example shown in FIGS. 3 and 4.

Additionally, in this example, some of the components are surface-mount components, and some of the components are through-hole components mounting to the PCB 400 by the component pins passing being located in a hole in the PCB. In other examples the components may all be surface-mount components, all through-hole components, or a different mix of these two types of components, or any other suitable type of component.

How the various components connect to each other is shown in the circuit diagram illustrated in FIG. 5. This shows the photodiode 402 and the various components that make up the analysis unit 432 connected to the photodiode.

The analysis unit 432 comprises three primary parts. These are a band pass filter 436, a comparator 438 and the output connector 430. The band pass filter 436 and the comparator 438 are each made up of a number of components. These components and how they are interconnected are described in more detail below.

The band pass filter 436 is an inverted active low pass filter. This is provided by the combination of an op-amp 412 and an RC circuit comprising a resistor 416 and a capacitor 426. The resistor and capacitor are connected in parallel between the negative input of the op-amp and the output of the op-amp. In this example the resistor has a resistance of 4.7 Mega Ohms (MΩ), the capacitor has a capacitance of 0.1 micro farads (μf or uf) at 50 Volts (V) and the op-amp is an LMC6001 op-amp, which is a current amplifier op-amp. In other examples, alternative components may be used.

The photodiode 402 is connected between the positive and negative input terminals of the op-amp 412 of the band pass filter 436. This acts as a resistor connected to the negative input of the op-amp as well as the source of signal across the positive and negative inputs (i.e. the input terminals) of the op-amp. The cathode of the photodiode is connected to the negative input of the op-amp and the anode of the photodiode is connected to the positive input of the op-amp.

In addition to the connection to the photodiode 402, the positive input of the op-amp 412 of the band pass filter 436 is also connected to ground. This is also the case for the negative voltage pin (V⁻) of the op-amp. The positive voltage pin (V⁺) of the op-amp is connected to a positive voltage supply, which, in this example, is a positive 5 V voltage supply.

The photodiode 402 of the example shown in FIGS. 3 to 5 is a SG01L-C18 photodiode. This is a UVC sensitive photodiode. The photodiode is a silicon carbide (SiC) based photodiode. Alternative photodiodes may be used in other examples.

The output of the op-amp 412 of the band pass filter 436, and therefore the output of the band pass filter, in this example, is connected to the comparator 438 and the output connector 430. The comparator is a voltage comparator based around an op-amp 414, a potential divider 440 and a pull-up resistor 444. In this example, the op-amp of the comparator is an LM393P op-amp, which is a dual differential comparator.

The positive input of the op-amp 414 of the comparator 438 is connected to the output of the op-amp 412 of the band pass filter 412. A resistor 418 is connected in the wiring 434 between the output of the op-amp of the band pass filter and the positive input of the op-amp of the comparator. In this example, this resistor has a resistance of 330Ω. This resistance may be different in other examples.

The negative input of the op-amp 414 of the comparator 438 is connected to the output 442 of the potential divider 440. The potential divider is provided by two resistors 420, 422 connected in series between a positive voltage source, which, in this example, is +5 V, and ground. The output of the potential divider is connected between the two resistors. The resistance of these resistors is determined by the individual characteristics of various components within the analysis unit 432 so is not shown in FIG. 5 since it may be different for each circuit.

The output 442 of the potential divider 440 acts as a reference voltage ($V_{ref}$) for the op-amp 414 of the comparator 438, and the output of the op-amp 412 of the band pass filter 436 acts as an input voltage ($V_{in}$) of the op-amp of the comparator.

The positive voltage pin of the op-amp 414 of the comparator 438 is connected to a +5 V supply. One end of a capacitor 428 is connected between the positive input of the op-amp of the comparator and the positive voltage supply. The other end of this capacitor is connected to ground. The negative voltage pin of the op-amp of the comparator is also connected to ground. In this example, the capacitor connected to the positive input of the op-amp of the comparator has a capacitance of 0.1 μf at 50 V.

The output of the op-amp 414 of the comparator 438 is connected to the output connector 430. The pull-up resistor 444 is connected between the output of the op-amp of the comparator and the output connector. The pull-up resistor is provided in this example by a resistor 424 that is connected at one end (an output end) to the connection between the op-amp of the comparator and the output connector, and at the opposing end to a positive voltage supply. This positive voltage supply is +5 V In this example, the resistance of the resistor of the pull-up resistor is 10 kΩ. In other examples, the positive voltage supply and/or the resistance of this resistor may be different.

The output connector 430 has multiple inputs. One of these inputs is connected to a positive voltage supply, which, in this example, is +5 V. Another of these inputs is connected to ground. In this example, there are two other inputs. One of these inputs is connected to the output of the band pass filter 436 as set out above. The other of these inputs is connected to the output of the comparator 438, which is provided by the combined output of the op-amp 414 of the comparator and the output of the pull-up resistor 444.

In relation to how the analysis unit functions, when UVC light is incident on the photodiode 402 at or above the threshold of 110 W/min over a 5 minute period, the current passing through the photodiode is maintained at a sufficiently high level that causes the impedance of the photodiode to be low. When the impedance of the photodiode is low, this lowers the cut-off frequency of band pass filter 436 since the capacitance of the capacitor 426 connected across the op-amp 412 of the band pass filter in parallel with the resistor 416 is kept constant. This blocks signal being passed through the band pass filter, which means no signal is provided from the output of the op-amp of the band pass filter. As such, only un-amplified signals are output from the band pass filter. Since these are un-amplified, any such signals are weak.

Any weak signal output from the band pass filter 436 passes to the output connector 430 and to the positive input of the op-amp 414 of the comparator 438. As the signal arriving at the positive input of the op-amp of the comparator is weak, the voltage provided as the $V_{in}$ voltage to the op-amp of the comparator will be lower than the $V_{ref}$ provided by the output 442 of the potential divider 440. This causes no signal to be output from the output of the op-amp of the comparator. This means that current flows from the pull-up resistor 444 to ground through the negative voltage pin of the op-amp of the comparator (since this is the path to ground of least resistance), and no signal passes to the output connector 430 from the comparator. This results in no signal being output by the output connector.

On the other hand, when UVC light is incident on the photodiode 402 below the threshold of 110 W/min over a 5 minute period, the current passing through the photodiode is low. This causes the impedance of the photodiode to be high. As a consequence of this the cut-off frequency of the band pass filter 436 is raised. Accordingly, a signal passes to the negative input of the op-amp 412 of the band pass filter. This signal is amplified by the op-amp of the band pass filter and output from the band pass filter.

As set out above, this amplified signal passes to the output connector 430. Additionally, the amplified signal passes to the positive input of the op-amp 414 of the comparator 436. The amplified signal provides a $V_{in}$ that is higher than the $V_{ref}$ provided by the potential divider 440. This causes the op-amp 414 of the comparator to output an amplified signal. Accordingly, there is a minimal potential difference between the output of the op-amp of the comparator and the pull-up resistor 444. As such, minimal current flows between the output of the op-amp of the comparator and the pull-up resistor. Instead, a current passes from the pull-up resistor to the output connector 430.

Since a signal is provided to the output connector 430, this signal is passed from the output connector out of the analysis unit 432. The output connector provides a connection to a control PCB (not shown). The control PCB is monitored by software running on the control system (not shown) of the analyser 1. As such, when the photodiode 402 output falls below the threshold, the generated signal is detected by the software running on the control system. The software in turn acts to inform a user of action being needed. In this example, the action needed is for the UVC bulb to be replaced to re-establish a suitable amount of UVC radiation being emitted to provide effective sterilisation.

The user may be informed through a user interface (not shown) on the analyser or by some other form or notification or alert. As an alternative to using software and/or a user interface, the signal output from the analysis unit 432 may be sufficient to notify a user, for example by causing a notification light to become illuminated. This allows the user to be informed of action being needed without software being needed.

The invention claimed is:

1. A sterilisation monitoring device for a molecular diagnostics analyser, the sterilisation monitoring device comprising:
a sensor arranged in use to detect ultraviolet radiation; and
an analysis unit connected to the sensor, the analysis unit comprising:
an inverted active low pass filter and a comparator, the sensor being connected at an input to the active low pass filter and an output of the active low pass filter being connected to an input of the comparator, the comparator being a voltage comparator and comprising a potential divider, an op-amp to which the potential divider and the output of the active low pass filter are connected, a pull-up resistor to which an output of the op-amp is connected, and an output to which the output of the op-amp and the pull-up resistor are connected, wherein
the analysis unit is arranged in use to issue a signal from the output of the comparator when the ultraviolet radiation level incident on the sensor is lower than a threshold level.

2. The sterilisation monitoring device according to claim 1, wherein the low pass filter is an RC filter.

3. The sterilisation monitoring device according to claim 1, wherein the comparator is a dual differential comparator.

4. The sterilisation monitoring device according to claim 1, wherein the sensor is a light sensor.

5. The sterilisation monitoring device according to claim 4, wherein the light sensor is an irradiance sensor.

6. The sterilisation monitoring device according to claim 4, wherein the threshold level is 110 Watts per minute (W/min) over a period of about 5 minutes.

7. A system for a molecular diagnostics analyser, the system comprising:
a sterilisation monitoring device comprising:
a sensor arranged in use to detect ultraviolet radiation; and
an analysis unit connected to the sensor, the analysis unit comprising:
an inverted active low pass filter and a comparator, the sensor being connected at an input to the active low pass filter and an output of the active low pass filter being connected to an input of the comparator, the comparator being a voltage comparator and comprising a potential divider, an op-amp to which the potential divider and the output of the active low pass filter are connected, a pull-up resistor to which an output of the op-amp is connected, and an output to which the output of the op-amp and the pull-up resistor are connected, wherein
the analysis unit is arranged in use to issue a signal from the output of the comparator when the ultraviolet radiation level incident on the sensor is lower than a threshold level; and
a decontaminator comprising a ultraviolet radiation source, wherein the ultraviolet radiation source is arranged to emit ultraviolet radiation in use in a distribution area,
wherein the sensor of the sterilisation monitoring device is positioned in the distribution area so as to receive ultraviolet radiation from the radiation source.

8. The system according to claim 7, wherein the ultraviolet radiation source is an ultraviolet type C (UVC) source.

9. A sample analyser for conducting a molecular diagnostic assay, the analyser comprising:
a processing region; and
a decontaminator comprising a ultraviolet radiation source mounted within the processing region, the ultraviolet radiation source being arranged to emit ultraviolet radiation in use in a distribution area to irradiate at least a portion of the processing region when in use; and
a sterilisation monitoring device having a sensor arranged in use to detect ultraviolet radiation, the sensor being located on a surface of the processing region in the at least a portion of the processing region able to be irradiated by the ultraviolet radiation source, the device further having an analysis unit connected to the sensor, the analysis unit comprising:
an inverted active low pass filter and a comparator, the sensor being connected at an input to the active low pass filter and an output of the active low pass filter being connected to an input of the comparator, the comparator being a voltage comparator and comprising a potential divider, an op-amp to which the potential divider and the output of the active low pass filter are connected, a pull-up resistor to which an output of the op-amp is connected, and an output to which the output of the op-amp and the pull-up resistor are connected, wherein the analysis unit is arranged in use to issue a signal from the output of the comparator when the ultraviolet radiation level incident on the sensor is lower than a threshold level.

10. The sample analyser according to claim 9, wherein the decontaminator is moveable within the processing region.

\* \* \* \* \*